United States Patent [19]
Koyfman et al.

[11] Patent Number: 5,393,594
[45] Date of Patent: Feb. 28, 1995

[54] ABSORBABLE NON-WOVEN FABRIC

[75] Inventors: Ilya Koyfman, Orange; Matthew Hain, New Haven, both of Conn.

[73] Assignee: United States Surgical Corporation, Norwalk, Conn.

[21] Appl. No.: 132,602

[22] Filed: Oct. 6, 1993

[51] Int. Cl.$^6$ .............................. D03D 3/00
[52] U.S. Cl. .................... 428/224; 428/284; 428/288; 428/300; 528/354
[58] Field of Search ............ 428/288, 300, 224, 284; 528/354

[56] References Cited

U.S. PATENT DOCUMENTS

| | | |
|---|---|---|
| 3,739,773 | 6/1973 | Schmitt et al. |
| 3,875,937 | 4/1975 | Schmitt et al. |
| 3,937,223 | 2/1976 | Roth . |
| 3,960,152 | 6/1976 | Augurt et al. |
| 3,988,411 | 10/1976 | Capozza . |
| 4,033,938 | 7/1977 | Augurt et al. |
| 4,074,366 | 2/1978 | Capozza . |
| 4,074,713 | 2/1978 | Capozza . |
| 4,128,612 | 12/1978 | Roth . |
| 4,135,622 | 1/1979 | Glick . |
| 4,549,545 | 10/1985 | Levy . |
| 4,578,067 | 3/1986 | Cruz, Jr. |
| 4,882,162 | 11/1989 | Ikada et al. |
| 4,916,193 | 4/1990 | Tang et al. |
| 4,950,483 | 8/1990 | Ksander et al. |
| 5,041,138 | 8/1991 | Vacanti et al. |
| 5,061,281 | 10/1991 | Mares et al. |
| 5,066,772 | 11/1991 | Tang et al. |
| 5,080,665 | 1/1992 | Jarrett et al. |
| 5,232,648 | 8/1993 | Kennedy et al. ........... 528/354 |
| 5,236,447 | 8/1993 | Kubo et al. |

FOREIGN PATENT DOCUMENTS 0325195 7/1989 European Pat. Off.
2222954 3/1990 United Kingdom .
WO92/10218 6/1992 WIPO .

OTHER PUBLICATIONS

Malm et al., Prevention of postoperative pericardial adhesions by closure of the pericardium with absorbable polymer patches, The Journal of Thoracic and Cardiovascular Surgery, vol. 104, No. 3, pp. 600–607, Sep. 1992.
Ethisorb ® 710 Pledgets (Product literature).
Nakamura et al., Bioabsorbable Non-Woven Fabric for Surgery, Medical Textiles for Implantation, Planck, Danner and Renardy Eds. pp. 329–332 (1990).
Nakamura et al., New Bioabsorbable Pledgets and Non-woven Fabrics Made from Polyglycolide (PGA) for Pulmonary Surgery: Clinical Experience, Thorac. cardiovasc. Surgn. 38 (1990) 81–85.
Nakamura et al., Clinical Applications of Bioabsorbable PGA Sheets for Suture Reinforcement and Use as Artificial Pleura, Japan Lung Surgery Journal 40: 10. 8 (1826) 1992 w/translation.

*Primary Examiner*—James J. Bell

[57] ABSTRACT

A low density bioabsorbable non-woven fabric is disclosed. The fabric preferably includes fibers of glycolide and lactide and has a density of between about 0.05 g/cu.cm and about 0.10 g/cu.cm. In one embodiment, the glycolide content of the fibers is at least about 80 mole percent, and preferably about 90 mole percent. In an alternate embodiment, the glycolide content of the fibers is less than 30 mole percent, and preferably about 20 mole percent.

17 Claims, 2 Drawing Sheets

ABSORBABLE NON-WOVEN FABRIC

BACKGROUND OF THE INVENTION

1. Field of the Invention

The present invention relates to non-woven fabrics, and more particularly, to bioabsorbable non-woven fabrics for use in medicine and surgery.

2. Description of the Related Art

Non-woven fabrics are porous, textile-like materials, usually in flat sheet form, composed primarily or entirely of fibers assembled in webs. Non-woven fabrics are also known as bonded fabrics, formed fabrics, or engineered fabrics and are manufactured by processes other than spinning, weaving or knitting.

The basic structure of non-woven fabrics is based on arrangements of fibers. Individual fibers are typically arranged more or less randomly. The tensile, stress-strain, and tactile properties of the non-woven fabric ordinarily stem from fiber to fiber friction created by entanglement and reinforcement of yarns, scrims, nettings and/or adhesive or other chemical and physical bonding.

Various methods are known for production of non-woven fabrics and include such procedures as crimping of multifilament yarn, cutting of yarn into staple fibers, carding of staple fibers, air laying, wet forming, spun-bonding, spunlacing, needlepunching and stitchbonding. Such procedures are discussed generally in the Encyclopedia of Polymer Science and Engineering, Vol. 10, pp. 204–253 (1987) incorporated herein by reference. These methods and others are used to produce non-woven fabrics from a variety of polymeric materials.

Certain non-woven fabrics have been used in medicine and surgery as all-purpose pads, pledgets, wound dressings, sponges, hemostats and the like. Bioabsorbable polymers such as lactide, glycolide and dioxanone have been incorporated in non-woven fabrics when contact with a wound or implantation into a patient's body is a possibility. In U.S. Pat. No. 3,875,937 polyglycolic acid is described as being fashioned into sterile gauze, felt or velour dressing and used to protect a wound surface or as a bolster to prevent a suture from cutting into tissue. However, no guidance is given relative to any procedures or specifications for forming such a non-woven fabric. U.S. Pat. Nos. 3,937,223 and 4,128,612 describe compacted surgical hemostatic felt and making absorbable felt from polyglycolic acid or a polymer having an ordered configuration of glycolic units and lactic acid units, or poly(N-acetyl-D-glucosamine). The hemostatic felt is described as produced by random formation by air scattering of a felt followed by heat embossing. Heat embossing appears to be a crucial aspect of the hemostatic felt, i.e., heat embossing and compacting fibers on the tissue contacting surface of the hemostat is stressed and said to aid in causing the felt to adhere sufficiently closely to hold the felt to the wound, and compacting the free surfaces reduces the tendency for blood to flow through the felt.

Bioabsorbable pledgets made from non-woven fabrics are described by Nakamura et al. in Thorac. Cardiovasc. Surg. pp. 81–85 (1990) and Medical Textiles For Implantation pp. 329–332 (1990) for use in cardiovascular and pulmonary surgery. The pledgets are said to be used to reinforce suture points and stop leakage from needle holes. However, few details relating to the production of the fabrics are provided. Commercially available resorbable pledgets, i.e., Ethisorb-710 (available in Germany from Ethicon, Inc.) are made of an absorbable composite material consisting of polyglactin and polydioxanone. Fibers of polyglactin and polydioxanone are welded together by means of heat and pressure to form pledgets.

Thus, it is seen that non-woven fabrics may be used in medicine for a variety of purposes. Properties of non-woven fabrics can be varied depending on constituent materials and the manufacturing process. Desirable characteristics of a bioabsorbable non-woven fabric include strength retention as measured by needle pull out, ease of needle penetration (both wet and dry) and low density. Low density is preferable for bioabsorbable implants since, for a given volume of implant, less material needs to be absorbed by the body. As density decreases, however, strength per unit volume typically decreases.

Therefore, the need exists for a reproducible superior low density bioabsorbable non-woven fabric which has requisite strength retention in the body. A need also exists for a low cost and simple method of manufacturing low density bioabsorbable fabrics.

SUMMARY OF THE INVENTION

The present invention provides a low density bioabsorbable non-woven fabric. The fabric includes fibers of glycolide and lactide and has a density of between about 0.05 g/cu.cm and about 0.10 g/cu.cm. In one preferred embodiment of the present invention, the glycolide content of the fibers is at least about 80 mole percent, and preferably about 90 mole percent. In an alternate embodiment, the glycolide content of the fibers is less than 30 mole percent, and preferably about 20 mole percent. However, the scope of the present invention is not limited to any particular ratio of glycolide and lactide.

The present invention also discloses a process for fabricating a low density bioabsorbable non-woven fabric. The process includes the steps of providing a bioabsorbable polymer, spinning the polymer into filaments, combining the filaments into a multifilament yarn, crimping the yarn using a "stuffer box", cutting the crimped yarn into staples, carding the staples to form a web and needle punching the carded web to form non-woven fabric.

Surprisingly, the fabric manufactured in accordance with the present invention has both a low density, i.e. of between about 0.05 g/cu.cm and about 0.10 g/cu.cm. and good initial strength with an improved strength loss profile over time. The resulting fabric also exhibits low needle penetration, which is particularly useful when the surgeon must penetrate the fabric during a surgical procedure. Additionally, the process for manufacturing the fabric is relatively simple compared to processes previously disclosed and currently being used in industry.

BRIEF DESCRIPTION OF THE DRAWINGS

Preferred embodiments of the invention are described hereinbelow, wherein.

DETAILED DESCRIPTION OF THE PREFERRED EMBODIMENTS

Figure 1:
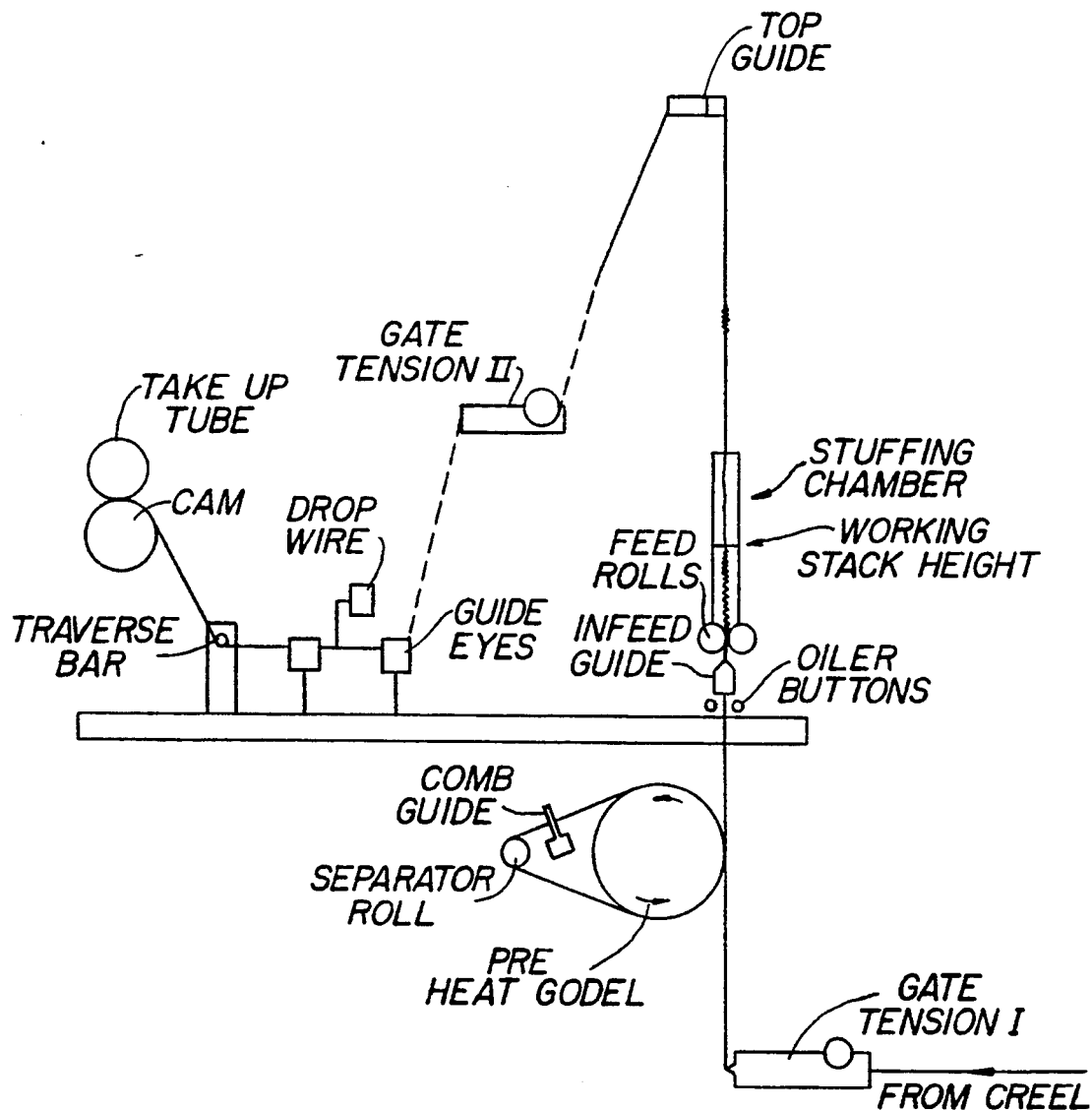
FIG. 1 is a diagram of a stuffer box/crimper suitable for processing filaments used in the present invention.

The following embodiments are examples of a low density bioabsorbable fabric which has surprisingly high in-vitro strength retention. In one embodiment of the present invention, the low density bioabsorbable non-woven fabric is manufactured from a 92.5/7.5 (mole percent) glycolide/lactide polymer yarn. The polymer is spun and drawn into a 69 filament 14 ply multifilament yarn of about 1.6 denier per filament. The 14 plyes are combined together by using a creel and a constant speed winder to prepare 1541 denier plied yarn. The yarn is crimped into a stuffer box according to the preferred specifications shown in Table I, below, with reference to FIG. 1.

TABLE I

| Crimping Conditions | Stufferbox Crimper |
| --- | --- |
| No. of yarn ends feeding from creel: | 1 |
| Total Yarn denier: | 1545 (14 ply × 69 filaments/yarn × 1.6 dpf) |
| Gate Tension 1 Setting: | 4 |
| Godet Setup: | |
| No. of wraps on the preheat godet: | 19 |
| Pre-heat Godet Set Temp: | 108° |
| Pre-heat Godet Indicating Temp: | 110° |
| Speed | 31 meters/minute |
| Infeed Gears (adjust's infeed yarn tension): | 48 × 18 |
| Stuffer Chamber Setup: | |
| Column Temp. Set Point (back only): | 96° C. |
| Indicating Temp. of Column: 8" glass column front | 99° C. |
| Working Stack Height in Column: | 6.5" to 7.5" |
| Take up gears (adjusts column stack height): | 26 × 15 |
| Gate Tension II Setting: | 0.5 |
| Crimp Analysis: | |
| Average No. of Crimps/inch: | 23.7 |
| Range (Min./Max.) | 16/36 |

The crimped yarn is cut into staples having fibers ranging from about 2–2.50 inches with an average length of about 2.25 inches. The staples are then carded to form a web. Prior to web formation, the staple fibers are passed through the card once to open the fibers. After opening, approximately 55 grams of opened fibers are used to produce a carded web having a basis weight of approximately 100 g/m², with dimensions of about 0.22 m × about 1.9 m. The carding specifications are shown in Table II.

TABLE II

| Carding 12" metallic card with variable speed control | |
| --- | --- |
| Card Conditions | |
| Main Cylinder Speed: | 186–188 rpms |
| Worker Cylinders: | 21–22 rpms |
| Stripper Cylinders: | 335 rpms |
| Take-off Apron: | 53 rpms |

From about one to about four carded web layers are then cross-lapped and needle-punched twice to form the bioabsorbable non-woven fabric. All web layers are combined during the first needle-punch pass. The second needle-punch pass is "dry", i.e., no webs are added. The first needle-punch pass involves the face fabric direction with about 320 needle penetrations per square inch to a depth of about 4 mm. The second needle-punch pass involves the back fabric direction with about 320 needle penetrations per square inch to a depth of about 8 mm. Certain other needling parameters are shown in Table III.

TABLE III

| Needling: 12" James Hunter Fiberlocker | |
| --- | --- |
| Needling Parameters | |
| Needle Type: | Groz Beckert, GB 30's 15 × 18 × 36 × 3 Barb Types: F333; G92919 |
| Needling Rate: | 120 strokes/minute |
| Needling Board Density: | 46 needles/linear inch |

When using two carded web layers, the resulting non-woven fabric is about 0.5 meters wide, less than about 2.5 mm thick and has a density of between about 0.05 g/cu.cm and about 0.10 g/cu.cm. Preferably, the density is between about 0.065 g/cu.cm and about 0.085 g/cu.cm. The basis weight of the fabric depends on the number of carded web layers needled together. Each carded web layer has a basis weight of between about 50 g/sq.m and about 100 g/sq.m. Preferably, the carded web layer basis weight is about 80 g/sq.m. The basis weight of a two layer fabric, for example, is between about 100 g/sq.m and about 200 g/sq.m and preferably about 160 g/sq.m. Optionally, the fabric can be coated or filled with various storage stabilizing agents, such as those disclosed in commonly assigned U.S. Pat. No. 5,032,429, the contents of which are incorporated herein by reference. Such storage stabilizing agents can include, for example, glycerol and calcium lactate.

The process in accordance with the present invention is quite simple as compared to those previously disclosed and currently used in industry. For example, U.S. Pat. Nos. 3,937,223 and 4,128,612 describe compacted surgical hemostatic felt and making absorbable felt from polyglycolic acid or a polymer having an ordered configuration of glycolic units and lactic acid units, or poly(N-acetyl-D-glucosamine). The hemostatic felt is described as produced by random formation by air scattering of a felt followed by heat embossing. Heat embossing is an additional step which fuses the felt fibers and contributes to the felt's density.

Ethisorb-710 (available from Ethicon, Inc.) are commercially available resorbable pledgets. The pledgets are made of an absorbable composite material consisting of polyglactin and polydioxanone. Fibers of polyglactin and polydioxanone are welded together by means of heat and pressure to form pledgets. The process of welding is an additional step which fuses the felt fibers and contributes to the felt's density.

The following table compares the absorbable non-woven fabric manufactured in accordance with the present invention to Ethisorb-710 (see background):

TABLE IV

| | Sample | Ethisorb-710 |
| --- | --- | --- |
| Thickness (mm) | 2.20 | 1.30 |
| Density (g/cu. cm) | 99.9 | 487 |
| Suture Pull Out (kg) | 14.4 | 18.68 |
| Needle Penetration (g) | | |
| Dry | 11.5 | 191.6 |
| Wet | 2.55 | 109.3 |

The suture pull out test was performed on 15×30 mm samples with three size 3-0 Polysorb ® sutures (available from United States Surgical Corporation) being equally spaced on the 30 mm side, 4 mm into the fabric. The sample was secured in the top grip and the sutures in the bottom grip of an Instron Model 1011 tensile tester. The tester was run at a crosshead speed of 50.0 mm/min until the sample failed. The needle penetration test was performed using an Instron Model 4301 with a 2000 g load cell. A CV-25 tapered needle (available from United States Surgical Corporation) was used for penetration.

Figure 2:
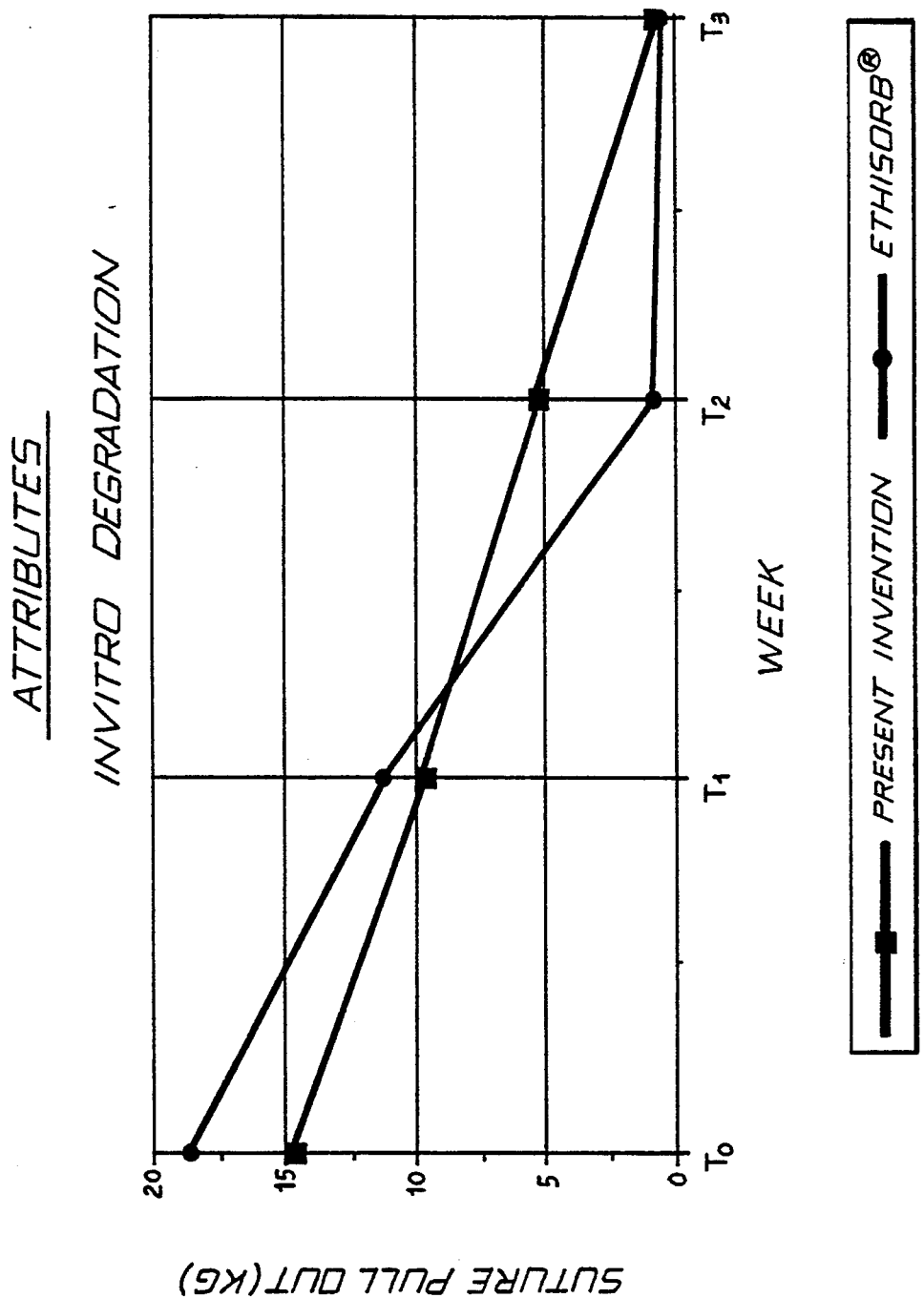
FIG. 2 compares in-vitro strength retention of the absorbable non-woven fabric of the present invention to another commercially available absorbable non-woven fabric.

In-vitro strength retention (Sorrenson's buffer at 37° C. over time) was measured at 0 weeks, 1 week, 2 weeks and 3 weeks. Comparative data to Ethisorb-710 is illustrated in FIG. 2. As can be seen, the fabric of the present invention looses strength more slowly than Ethisorb-710 and has greater strength at week 2. At week 3, both fabrics essentially loose all strength. Since Ethisorb-70 has almost five times the density as the fabric of the present invention, the relatively high week 2 strength retention of the now-disclosed fabric is quite unexpected.

The present invention, therefore, provides surgeons with a high-strength/low-mass implant which avoids the need for the body to absorb relatively higher quantities of foreign material. This is particularly advantageous when the foreign material is at least partially fabricated from acid polymers, i.e. glycolic and/or lactic acid, wherein breakdown of the polymer results in pooling of acid in the body. Localized acid pooling may cause tissue trauma or irritation. As such, since the fabric of the present invention decreases implant mass, the invention also reduces the risk of tissue irritation and/or trauma.

In an alternative embodiment of the present invention, the bioabsorbable non-woven fabric is manufactured from a 18/82 (mole percent) glycolide/lactide polymer yarn. Filaments for this embodiment can be manufactured in accordance with methods disclosed in commonly assigned U.S. Pat. No. 5,232,648, the contents of which is incorporated herein by reference. The filaments exhibit excellent in-vivo strength retention and can be further processed to form a non-woven fabric, as described above.

Further process steps for manufacturing an absorbable non-woven fabric in accordance with the present invention can include the following:

two web layers (total 200 g/m$^2$) are needled together to form a fabric;
the fabric is washed in water for 5 min. and dried in vacuum;
the fabric is post treated at 90° C. for 16 hours;
the fabric is platen pressed at 90° C., 12 sec. with 0.020" shims;
the fabric is postwashed in water for 5 min. and dried in vacuum;
the fabric is then cut to size, packaged and Ethylene Oxide sterilized.

Surgical pledgets made from any of the above-described fabrics can be used in conjunction with surgical sutures and needles to distribute the tension caused by the interaction of sutures with body tissue over at least a portion of the pledget. The pledgets may be rectangular, circular, ellipsoidal or polygonal.

Surgical bolsters made from any of the above-described fabrics can be used in conjunction with surgical sutures and needles to distribute the tension caused by the interaction of sutures with body tissue over at least a portion of the bolster. The bolsters may be rectangular, circular, ellipsoidal or polygonal.

While this invention has been disclosed herein in connection with certain embodiments and procedural details, it is clear that changes, modifications or equivalents can be used by those skilled in the art. For example, while fibers of glycolide and lactide have been disclosed in connection with the preferred embodiments, other bioabsorbable polymers can be used to produce a low density fabric in accordance with the present invention. Such bioabsorbable polymers can include, for example, p-dioxanone, α-caprolactone and trimethylene carbonate. Accordingly, changes within the principles of this invention are intended to be included within the scope of the claims below.

What is claimed is:

1. A bioabsorbable non-woven fabric including fibers comprising glycolide and lactide, said non-woven fabric having a density of between about 0.05 g/cu.cm and about 0.10 g/cu.cm.

2. The bioabsorbable non-woven fabric of claim 1, wherein said fabric has a basis weight of between about 50 g/sq.meter and about 400 g/sq.meter.

3. The bioabsorbable non-woven fabric of claim 2, wherein said fabric has a basis weight of about 160 g/sq.meter.

4. The bioabsorbable non-woven fabric of claim 1, wherein the glycolide content of said fibers is at least about 80 mole percent.

5. The bioabsorbable non-woven fabric of claim 4, wherein said fibers comprises a copolymer of glycolide and lactide and the glycolide content of said fibers is about 90 mole percent.

6. The bioabsorbable non-woven fabric of claim 1, wherein the glycolide content of said fibers is less than about 30 mole percent.

7. The bioabsorbable non-woven fabric of claim 6, wherein said fibers comprises a copolymer of glycolide and lactide and the glycolide content of said fibers is about 20 mole percent.

8. The bioabsorbable non-woven fabric of claim 1 having a dry needle penetration value of less than 20 grams.

9. The bioabsorbable non-woven fabric of claim 8 having a dry needle penetration value of less than 15 grams.

10. The bioabsorbable non-woven fabric of claim 1 having a wet needle penetration value of less than 10 grams.

11. The bioabsorbable non-woven fabric of claim 9 having a wet needle penetration value of less than 5 grams.

12. The bioabsorbable non-woven fabric of claim 1, further comprising a storage stabilizing agent.

13. The bioabsorbable non-woven fabric of claim 12, wherein said storage stabilizing agent is glycerol.

14. The bioabsorbable non-woven fabric of claim 1 fabricated from a plurality of carded web layers.

15. The bioabsorbable non-woven fabric of claim 14 fabricated from 2 to 4 carded web layers.

16. The bioabsorbable non-woven fabric of claim 1, wherein said fabric retains at least about 20 percent of its original strength after three weeks in saline solution, said strength being measured as a function of suture pull out.

17. The bioabsorbable non-woven fabric of claim 16, wherein said fabric retains at least about 30 percent of its original strength after three weeks in Sorrinson's buffer, said strength being measured as a function of suture pull out.

* * * * *